United States Patent [19]

Shalaby et al.

[11] 4,186,189
[45] Jan. 29, 1980

[54] ABSORBABLE PHARMACEUTICAL COMPOSITIONS BASED ON POLY(ALKYLENE OXALATES)

[75] Inventors: Shalaby W. Shalaby, Long Valley; Dennis D. Jamiolkowski, Paterson, both of N.J.

[73] Assignee: Ethicon, Inc., Somerville, N.J.

[21] Appl. No.: 837,076

[22] Filed: Sep. 28, 1977

[51] Int. Cl.$^2$ .................... A61K 31/74; A61K 9/32; A61K 9/22; A61K 9/52
[52] U.S. Cl. ...................................... 424/78; 424/19; 424/32; 528/272
[58] Field of Search ................ 424/78, 19, 32; 528/272

[56] References Cited

U.S. PATENT DOCUMENTS

| | | | |
|---|---|---|---|
| 2,012,267 | 8/1935 | Carothers | 528/272 |
| 2,071,250 | 2/1937 | Carothers | 260/106 |
| 2,071,251 | 2/1937 | Carothers | 18/54 |
| 2,111,762 | 3/1938 | Ellis | 260/8 |
| 2,952,652 | 9/1960 | Beindorff | 260/30.6 |
| 3,755,558 | 8/1973 | Scribner | 424/47 |
| 3,773,919 | 11/1973 | Boswell et al. | 424/19 |
| 3,883,901 | 5/1975 | Coqvard et al. | 528/272 |
| 3,978,203 | 8/1976 | Wise | 424/32 |
| 3,997,512 | 12/1976 | Casey et al. | 260/75 R |
| 4,105,034 | 8/1978 | Shalaby et al. | 424/19 |
| 4,130,639 | 12/1978 | Shalaby et al. | 424/78 |

OTHER PUBLICATIONS

Carothers et al., J. Am. Chem. Soc., 52, 3292, (1930).
Alksnis et al., J. Polym. Sci., Polym. Chem. Ed., 15, 1855, (1977).
Savinov et al., Polym. Sci., U.S.S.R., 6, 1475, (1964).

*Primary Examiner*—Donald B. Moyer
*Attorney, Agent, or Firm*—Wayne R. Eberhardt

[57] ABSTRACT

Absorbable polymers derived from alkylene oxalates are formulated with drugs and introduced into the body to provide a slow, sustained release of the drug over an extended period of time in accordance with the rate of absorption of the polymer. Polymers of alkylene oxalates, particularly wherein the alkylene moiety is $C_3$ to $C_{16}$, are biodegradable in animal tissue and absorb with minimal adverse tissue reaction.

13 Claims, No Drawings

ABSORBABLE PHARMACEUTICAL COMPOSITIONS BASED ON POLY(ALKYLENE OXALATES)

BACKGROUND OF THE INVENTION

1. Field of the Invention

This invention relates to novel polymer-drug compounds and their use in providing sustained release drug delivery to human and other warm-blooded animals. The polymer-drug compounds provide a mechanism whereby the rate of release and availability of the drug may be regulated so that the quantity of a drug which is released at a particular time or at a particular site is relatively constant and uniform over extended periods of time.

2. Description of Prior Art

Drugs are conventionally administered orally or via injection, often at a site remote from the target. Over a relatively short period of time, the drug diffuses into the circulation system of the patient and is distributed to the various organs, at least one of which is the intended target for the drug. The action of the drug on organs other than the target may result in undesirable side effects. Finally, the drug is metabolized or otherwise irreversibly removed from the organism by excretion or chemical deactivation.

When drugs are delivered orally or by injection, the level and duration of availability of the drug cannot be controlled independently; only the size and frequency of the dose can be manipulated. Typically, there is an initially high concentration of available drug at the site of injection or in the circulatory system which then decreases gradually as the drug is distributed and consumed within the body of the patient.

In controlled sustained delivery, a formulation of the drug and a carrier is administered to the patient by injection or implantation. The carrier forms a drug reservoir that protects the stored drug from extraneous removal mechanisms and releases the drug to the biological reservoir at a predetermined rate. Controlled sustained delivery of a drug prevents undesirable peaking of blood levels and makes the drug available at an optimum and uniform concentration over an extended period of time. Only the released drug is subject to removal via metabolism and excretion.

U.S. Pat. Nos. 3,773,919, 3,755,558, and 3,997,512 describe formulations of various polylactides, polyglycolides and copolymers of glycolide and lactide with some well-known drugs in order to achieve slow release of the drugs when implanted or applied topically to humans. These compositions are designed to release the drug over an extended period of time as the polymer of the mixture is slowly absorbed in the system. The polymer itself is nonreactive to body tissue and degrades into harmless products which are metabolized or excreted by the host body.

We have discovered that polymers of alkylene oxalate are also absorbed slowly in animal tissue without significant adverse tissue reaction.

Polymers of poly(alkylene oxalates) and the preparation thereof are described in the art. Carothers et al, J. Amer. Chem. Soc. 52, 3292 (1930), for example, describes the ester interchange reaction of diols such as ethylene glycol, 1,3-propanediol, or 1,4-butanediol with diethyl oxalate to yield a mixture of monomer, soluble polymer and insoluble polymer. The reaction of oxalic acid and an alkylene glycol to form polyester resins is described in U.S. Pat. No. 2,111,762, while the preparation of polyesters of fiber-forming quality from dicarboxylic acids and diols is described in U.S. Pat. No. 2,952,652. The reaction of ethylene glycol with oxalic acid to form fiber-forming polymer was described recently in J. Polym. Sci., Polym. Chem. Ed., 15, 1855 (1977). Superpolyesters of fiber-forming quality and derived from dibasic acids plus glycols are described in U.S. Pat. Nos. 2,071,250 and 2,071,251. Linear polyesters of oxalic acid have been reported as having high melting points, being soluble in many solvents, capable of forming films, and readily hydrolyzed [Savinov et al, Polym. Sci. USSR 6, 1475 (1964)].

There was, however, no appreciation in the prior art of the absorbability of poly(alkylene oxalate) polymers in animal tissue, and no suggestion for the use of poly(alkylene oxalate) polymers in surgical applications. In particular, there has been no suggestion in the art to utilize polymers of alkylene oxalates in the preparation of absorbable polymer-drug compositions in accordance with the present invention.

SUMMARY

Pharmaceutical depot compositions for parenteral administration of effective amounts of drugs over an extended period of time comprise mixtures and combinations of one or more drugs with absorbable polymers of alkylene oxalate. The polymers are conveniently prepared by known polymerization techniques. Polymers and drugs are utilized as physical mixtures or as chemically bonded compounds. The polymer-drug composition may be administered to the patient by implantation as a solid pellet, by injection as a suspension in a biologically acceptable fluid, or by other convenient means.

DESCRIPTION OF THE INVENTION

The formulations of this invention are absorbable, non-irritating pharmaceutical compositions consisting of one or more drugs intimately mixed with or chemically bonded to an absorbable polymer. When implanted in an animal system, effective amounts of the drug are released at a predetermined rate over an extended period of time as the polymer is absorbed in the system. The invention is of particular value for drugs that require prolonged administration as, for example, certain fertility-control drugs or hormones used for hormone-replacement therapy.

The novel formulations of the present invention permit the continuous release of drugs over an extended period of time from the sites of parenteral administration and minimize the frequency and thus the discomfort and inconvenience associated with conventional injection formulations. The poly(alkylene oxalate) polymers undergo biodegradation in the body into products which are nonreactive toward body tissue, and can be designed, by controlling molecular weight and composition, to undergo hydrolysis and release drug from the depot at a desired rate.

The Drug

The term "drug" is intended in its broadest sense as defined in the Federal Food, Drug and Cosmetic Act, Section 201(2)g:

(1) articles recognized in the official *United States Pharmacopoeia*, official *Homeopathic Pharmaco-* poeia of the United States, or official National Formulary, or any supplement of any of them; and (2) articles intended for use in the diagnosis, cure, mitigation, treatment, or prevention of disease in man or other animals; and (3) articles (other than food) intended to affect the structure or any function of the body of man or other animals; and (4) articles intended for use as a component of any article specified in clauses 1, 2 or 3; but does not include devices or their components, parts, or accessories.

Classes of drug which may be specifically mentioned include agents affecting the central nervous system, e.g., narcotics, such as, for example, morphine; narcotic antagonists, such as naloxone; antipsychotic agents, such as chlorpromazine and molindone; antianxiety agents, such as sodium pentobarbital, antidepressants, such as imipramine hydrochloride; stimulants, such as methyl phenadate and nikethamide; hallucinogens; analgesics, such as numorphan, meperidine, and morphine; and anorexigenic agents.

Other classes are pharmacodynamic agents, e.g., antihypertensive agents as reserpine, and chlorisondamine chloride, and antianginal agents, such as papaverine, and drugs for therapy of pulmonary disorders, such as theophylline ethylenediamine salt and epinephrine. Additional classes are chemotherapeutic agents, e.g., antiviral; antiparasitic, such as emetine hydrochloride and stibophen; antifungal agents, such as cycloheximide; and antineoplastic agents, such as triethylene thiophosphoramide; agents affecting metabolic diseases and endocrine functions, e.g., prostaglandins; athersclerosins, such as heparin; steroids and biologically related compounds; polypeptides, such as bacitracin, polymixin B sulfate, and sodium colistimethate; natural and synthetic hormones, such as estradiol dipropionate, progesterone, and hydroxy progesterone caproate; steroid and nonsteriodal anti-inflammatory agents, such as gold sodium thiomalate and hydrocortisone sodium succinate; and agents affecting thrombosis, such as crystalline trypsin; vitamins, such as vitamin $B_{12}$; anti-epilepsy agents, such as phenobarbital; and the like. It should be understood that the specific drugs mentioned by name are illustrative and not limitative.

Endrocrine agents comprise a particularly useful class of compounds in this invention and can be defined either as natural hormones or as synthetic drugs that to some extent act like, or antagonize, natural hormones. Endocrine agents include, but are not limited to, both steroids and nonsteroids that function as fertility-control agents; progestogens, estrogens, androgens, antiandrogens, corticoids, anabolic agents, and anti-inflammatory agents.

Examples of specific endocrine agents that can be used in the formulations of the invention are set forth in U.S. Pat. No. 3,773,919, particularly Columns 3 to 7, which patent is incorporated herein in its entirety by reference.

The Absorbable Polymer

Polymers useful in the preparation of polymer-drug compounds of the present invention are comprised of units having the general formula:

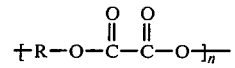

wherein R is a $C_3$ to $C_{16}$ alkylene, most preferably $C_4$ to $C_{10}$ alkylene, and n is the degree of polymerization resulting in a polymer having an inherent viscosity of at least 0.20 determined at 25° C. on a 0.1 g/dl solution of polymer in $CHCl_3$ or hexafluoroisopropanol.

Alkylene oxalate polymers of the present invention are conveniently prepared by an ester interchange reaction between an alkylene diol and a lower ester of oxalic acid in the presence of an ester interchange catalyst. The diol is preferably a $C_3$ to $C_{16}$ alkylene diol, and the ester of oxalic acid preferably diethyl oxalate. The ester interchange is preferably conducted in two stages wherein the reactants are first heated with stirring under a nitrogen atmosphere to form a prepolymer with the removal of ethanol, followed by postpolymerization under heat and reduced pressure to obtain a final polymer of the desired molecular weight.

The preparation of useful polymers of alkylene oxalate is further illustrated by the following examples. The following analytical methods were used to obtain the data reported in the examples. Inherent viscosity ($\eta_{inh}$) of polymer was determined at 25° C. on a 0.1 g/dl solution of polymer in chloroform or hexafluoroisopropynol (HFIP). A DuPont 990 DSC apparatus was used to determine the melting temperatures ($T_m$) of polymer in nitrogen, using a 4 mg sample and a heating rate of 10° or 20° C./min as specified. Crystallinity was determined by the method of Hermans and Weidinger and the diffractometer patterns were resolved with a DuPont 310 curve analyzer.

In vitro hydrolysis of polymer discs (about 1.2 g, 2.2 cm diameter) and monofilaments (8–25 mil) were conducted in a phosphate buffer of pH 7.25 at 37° C.

In vivo absorption (muscle) was demonstrated by melt extruding the polymer into filaments and implanting two 2 cm segments of a filament into the left gluteal muscles of female Long-Evans rats. The implant sites were recovered after periods of 60, 90, and 120 and 180 days and examined microscopically to determine the extent of absorption. In vivo absorption (subcutaneous) is a nonhistological technique in which continuous observation of the biological degradation of segments of the filament were made by implanting two filaments, 2 cm long, into the abdominal subcutis of young female rats. The implants are readily visible when the skin is wetted with propylene glycol and extent of absorption can be determined by subjective visual examination.

EXAMPLES

General Polymerization Procedure

Diethyl oxalate was heated with a selected diol in a mechanically-stirred reactor using a stannous alkanoate or an organic titanate as a catalyst. The reaction was conducted under a nitrogen atmosphere at suitable temperatures until a substantial portion of the calculated amount of ethanol was obtained. Postpolymerization of the resulting prepolymer was then continued under reduced pressure using a suitable heating scheme. At the end of the postpolymerization period, the molten polymer was allowed to cool slowly at room temperature, isolated, ground and redried at 25° to 80° C. (depending on the polymer $T_m$) in vacuo for at least one day. Detailed experimental conditions for the preparation of representative samples of linear polyalkylene oxalates and important properties of the resulting polymers are presented below.

EXAMPLE 1

Poly(trimethylene oxalate)

Distilled 1,3-propanediol (17.48 g, 0.23 mole) and diethyl oxalate (29.2 g, 0.2 mole) were mixed with a catalytic amount of stannous oxalate (4.1 mg, 0.02 mmole) under nitrogen. the mixture was heated with stirring while allowing the resulting ethanol to distill at 150°, 120° and 150° C. for 0.5, 2 and 4 hours, respectively. The resulting polymer was then cooled to about 100° C. and the pressure was reduced to 0.1 mm. The polymerization was continued in vacuo at 150°, 160°, 180° and 200° C. for 1, 3, 1 and 2 hours, respectively. The polymeric product was recovered as a clear, soft material.

Polymer Characterization $\eta_{inh}$ in $CHCl_3 = 0.57$;
DSC (20° C./min): $T_g = -1°$ C.

EXAMPLE 2

Poly(tetramethylene oxalate)

Diethyl oxalate (36.5 g, 0.25 mole) was mixed with 1,4-butanediol (45 g, 0.5 mole) and a 1 percent solution of tetrakis(2-ethylhexyl) titanate (TOT) catalyst (1 ml, 0.012 mmole) and transferred to a resin kettle under a dry nitrogen atmosphere. A prepolymer was formed by heating the reaction mixture under a nitrogen atmosphere for 2 hours each at 140° and 160° C. while allowing the formed ethanol to distill. The mixture was then heated under reduced pressure (2-3 mm Hg) at 160° and 180° C. for 20 and 2 hours, respectively. The polymer melt was slow-cooled, quenched in liquid nitrogen, isolated and ground. The ground polymer was redried at room temperature, in vacuo.

Polymer Characterization $\eta_{inh}$ in HFIP = 0.95
DSC (20° C./min): $T_g = 4.5$; $T_c = 22$; $T_m = 105°$ C.
In vivo properties: Subcutaneous implantation of 12.9 mil filaments in rats indicated that 50 percent of their apparent mass was absorbed in the first 9 days, and 10 percent remained after 15 days, and absorption was substantially complete after 28 days.

EXAMPLE 3

Poly(hexamethylene oxalate)

Distilled diethyl oxalate (73.1 g, 0.500 mole) was mixed with 1,6-hexanediol (61.2 g, 0.519 mole) and stannous octoate catalyst (0.33 M in toluene; 0.3 ml, 0.1 mmole) under a dry nitrogen atmosphere in a glass reactor equipped with a mechanical stirrer. A prepolymer was formed by heating the mixture at 120° C. for 2 hours and then at 160° C. for 3 hours under nitrogen at 1 atmosphere while allowing the formed ethanol to distill. The prepolymer was then heated for one hour in vacuo (0.1 mm Hg) at 80° and then 90° C. The postpolymerization of the polymer melt was completed by heating at 100°, 115°, 135°, 150°, 170°, 190° and 200° C. for 2, 1, 1.5, 4, 6, 1 and 6.5 hours, respectively. The polymer was allowed to cool at room temperature, quenched in liquid nitrogen, isolated and ground. The ground polymer was dried in vacuo at room temperature.

Polymer Characterization $\eta_{inh}$ in $CHCl_3 = 0.83$
DSC (10° C./min): $T_m = 70°$ C.
In vivo evaluation: Subcutaneous implantation of 8.7 mil filaments in rats indicated that absorption of the fiber was about 20% complete after 42 days, and that after 121 days absorption was substantially complete.

EXAMPLE 4

Poly(octamethylene oxalate)

Using a similar system to that of Example 3, distilled diethyl oxalate (109.6 g, 0.750 mole), distilled 1,8-octanediol (113.6 g, 0.777 mole) and stannous octoate catalyst (0.33 M in toluene - 0.455 ml, 0.150 mmole) were mixed under a dry nitrogen atmosphere in a glass reactor equipped with a mechanical stirrer. A prepolymer was formed by heating the mixture at 120° C. for 12 hours under nitrogen while allowing the formed ethanol to distill. Prior to postpolymerization, the product was heated for 1 hour at 90° C. and 0.1 mm Hg. The postpolymerization of the stirred polymer melt was completed by heating at 110°, 135°, 150°, 170° and 200° C. for 3.5, 2.5, 4.5, 0.5 and 5 hours, respectively at 0.1 mm Hg. The polymer was cooled, quenched in liquid nitrogen, isolated, ground and dried in vacuo at room temperature. The polymer was then heated at 60° C. in vacuo for one hour and finally at 200° C. for 6 hours to yield the final product.

Polymer Characterization $\eta_{inh}$ in $CHCl_3 = 0.88$
DSC (10° C./min): $T_m = 75°$ C.
In vivo evaluation: Filaments (8.8 mil) implanted into the gluteal muscles of rats showed no evidence of absorption up to the 42nd day. After 119 days, there was evidence of minimal absorption of some of the filaments.

EXAMPLE 5

Poly(decamethylene oxalate)

1,10-Decanediol (87.1 g, 0.5 mole) was mixed with diethyl oxalate (58.4 g, 0.4 mole) and a solution of TOT catalyst in toluene (0.012 mmole) under a nitrogen atmosphere. The reaction mixture was heated with stirring while allowing the resulting ethanol to distill at 120°, 130° and 140° C. for 4, 2.5 and 2 hours respectively. The pressure was then reduced to 0.5 mm while heating to 190° C. for 20 minutes. The polymerization was continued in vacuo at 190° and 210° C. for 4 and 13 hours, respectively. The polymer was recovered and characterized as follows:

Polymer Characterization $\eta_{inh}$ in $CHCl_3 = 0.45$
DSC (10° C./min): $T_m = 77.5°$ C.
In vitro hydrolysis data: Melt extruded filaments had a weight loss of 1, 11, 38 and 62 percent after 6, 17, 44 and 177 days, respectively.

EXAMPLE 6

Poly(dodecamethylene oxalate)

Distilled diethyl oxalate (14.6 g, 0.100 mole) was mixed with 1,12-dodecanediol (20.8 g, 0.103 mole) and stannous octoate catalyst (0.33 M in toluene - 0.061 ml, 0.02 mmole) under a dry nitrogen atmosphere in a glass reactor equipped for magnetic stirring. The prepolymer was formed after heating the mixture at 120° C. for 3 hours and 160° C. for 2 hours under nitrogen at 1 atmosphere while allowing the formed ethanol to distill. The mixture was then heated for 6 hours in vacuo (0.1 mm Hg) at 200° C. and then 210° C. for 2 hours. The postpolymerization of the polymer melt was completed after heating at 200° C. for 5 additional hours. The polymer was cooled at room temperature and recovered.

Polymer Characterization $\eta_{inh}$ in $CHCl_3 = 0.57$
DSC (20° C./min): $T_m = 91°$ C.

EXAMPLE 7

Poly(hexadecamethylene oxalate)

Using a similar system to that used for Example 6, diethyl oxalate (8.0 g, 0.055 mole), 1,16-hexadecanediol (14.6 g, 0.057 mole) and stannous octoate catalyst (0.33 M in toluene - 0.033 ml, 0.01 mmole) were mixed under an atmosphere of dry nitrogen in a glass reactor equipped for magnetic stirring. The prepolymer was formed after heating the mixture at 120° C. for 3 hours and then 160° C. for 2 hours under nitrogen at 1 atmosphere while allowing the formed ethanol to distill. The mixture was then heated in vacuo at 0.1 mm Hg and at 200°, 210° and 230° C. for 2, 2 and 3 hours, respectively. The postpolymerization of the stirred polymer melt was completed after heating at 200° C. for 4 additional hours. The polymer was cooled and recovered.

Polymer Characterization $\eta_{inh}$ in $CHCl_3 = 0.45$
DSC (20° C./min): $T_m = 95°$ C., $T_g = 40°$ C.

While the preceding examples have been directed to the preparation of specific homopolymers of poly(alkylene oxalates), these examples are for purposes of illustration only and are not limiting of the invention. Copolymers of $C_3$ to $C_{16}$ alkylene oxalate with up to about 50 percent by weight of one or more other monomers copolymerizable therewith to produce nontoxic and absorbable polymers, and physical mixtures of such homopolymers and copolymers, are likewise included within the present invention. For example, mixtures of poly(alkylene oxalate) with polymers of lactide and/or glycolide are useful in the preparation of compositions wherein the rate of absorption can be controlled by varying the relative proportions of the constituents.

Polymers of the present invention are adversely affected by moisture and are accordingly preferably prepared and stored in a substantially moisture free environment and in hermetically sealed packages. Polymers which have been dried under vacuum at elevated temperatures and subsequently stored under vacuum or in a dry nitrogen environment are found to be quite storage stable.

Preparation and Administration of Polymer-Drug Compositions

The drug and the polymer can be mixed, and the intimacy of mixing, particle size, and particle shape of the formulation can be varied, by any of a number of known methods. Intimacy of mixing, particle size, and particle shape of the formulations of the invention will depend to some extent on the intended use. High homogeneity can be obtained by mixing the components in the molten state, cooling, and grinding the resulting solid. A formulation so obtained is suitable for injection as $0.1\mu$ to $1000\mu$ particles suspended in saline solution or a pharmaceutically acceptable oil. In some cases particles with cores of pure drug coated with various thicknesses of polymer can be preferred for delayed and/or sustained release. Relatively large pellets (1-10 mm) may be preferred for reversible implantation in animals by surgery or by injection as projectiles. For this use adequate homogeneity can usually be realized by grinding or milling the drug and the polymer together before forming pellets under pressure. Known techniques of encapsulation, including microencapsulation, can be used to mix the polymer and the drug. The formulations of this invention provide a slow, steady release of drug in contradistinction to conventional preparations which generally produce a rapid surge followed by a fairly quick decline in drug effect.

Polymer-drug mixtures of the invention may contain pharmaceutically acceptable inert additives such as plasticizers. Typical plasticizers are Carbowax polyethylene glycols, glycerides and ethylcellulose.

The relative proportions of the drug and poly(alkylene oxalate) polymer can be varied over a wide range depending on the desired effect. Since the drug will be released over an extended period of time, the quantity of drug may be greater than the conventional single dose and the polymer must not break down or become absorbed by the body so rapidly as to release undue quantities of drug. The polymer-drug composition may range from 1 percent of drug and 99 percent of the polymer to 99 percent of drug and 1 percent of the polymer. Preferred compositions include 1 part of drug and from 4 to 20 parts of polymer.

These formulations can be injected as fluid suspensions by syringe into subcutaneous cellular tissue or muscular tissue, or implanted in pellet form subcutaneously or intramuscularly. Liquid vehicles useful for suspensions of the drug-polymer formulation include water or aqueous solutions such as normal sodium chloride solution or sodium carboxymethyl cellulose in water. Oils such as sesame oil or peanut oil containing, if desired, dissolved adjuvants such as benzyl alcohol, may also be used to prepare suspensions of the polymer-drug formulation.

Drug compounds of the classes mentioned earlier may be coated, embedded, or intimately mixed in or with a matrix of one or a combination of different chain-length biodegradable polymers to give a drug-polymer mixture which will provide a controlled sustained release of the drug compound over a period of 8 hours to 2 months or longer when administered parenterally.

Coating, embedding or intimately mixing the drug compound with the polymer can be accomplished in the following ways:

(A) Coating the discrete drug particles or drug-particle aggregates, agglomerates or flocs by:

(1) Spray drying: Finely divided drug particles are suspended in a solvent system in which the drug is not soluble containing the dissolved polymer and other agents, e.g., extenders, plasticizers, dyes, etc., in the drug/polymer ratio from 1/99 to 99/1, followed by spray drying. For example: Drug particles 0.2 to 10 microns in size and equal to the weight of polymer used are suspended in a solvent solution of polymer in such a concentration so as to give a liquid viscosity suitable for atomizing. The drug-polymer mixture is spray-dried using conventional methods of atomizing, e.g., centrifugal wheel, pressure, and two-fluid nozzle using appropriate drying conditions and temperatures that do not exceed the softening point of the polymer and do not exceed the melting point or decomposition point of the drug. Solvents useful in preparing solutions of the polymers of the present invention include, but are not limited to, hexafluoroisopropyl alcohol, hexafluoroacetone, trichloroethane, tetrachloroethane, trifluoroacetone, toluene, dichloroethane, chloroform, and methylene chloride.

(2) Pan coating or fluid-bed coating: Place granules or pellets, 5 microns to 20 mm, preferably between 0.25 and 10 mm diameter, in a rotating coating pan or fluid-bed drier, and apply polymer (dissolved in a carrier to a suitable viscosity for spraying) by spraying until a suitable coating quantity has been deposited to give the required release-rate characteristics. For example: granules of drug are prepared by extrusion of a wet granulation or other suitable methods known to the art, and dried. 16-to-40 Mesh granules are placed in a rotating coating pan and a solution of polymer, dissolved in a suitable nonaqueous volatile solvent, is sprayed onto the moving granules with a continuous fine spray under conditions known to the art, until a coating giving the desired release rate has been applied. The granules are then dried.

(3) Microencapsulation: Suspend drug particles, granules or pellets (0.1 to 2000 microns diameter) in a solvent system in which the drug is not soluble, and which contains the polymer in solution. Add an agent incompatible with the polymer-solvent system, such as an incompatible polymer, a nonsolvent for the polymer, or a salt, or vary conditions such as temperature and pressure. One or a combination of the above will precipitate the polymer, coating the drug particles, granules or pellets. For example: 0.5 to 25 micron drug particles are suspended in a low viscosity solution of the polymer in a suitable solvent in which the drug is not soluble. A miscible solvent in which the polymer is not soluble, such as hexane, is then added slowly to precipitate the polymer. The coated particles are filtered and washed with hexane and allowed to dry. The powder is stored for use in the suitable dosage form.

(B) Embedding

The polymer or polymer mixture is melted and a nonheatlabile drug is suspended and thoroughly dispersed in the melt. The melt is congealed by spraying, or in a mass and ground into small particles to give a polymer matrix with the drug embedded. For example: the poly(alkylene oxalate) polymer is melted and 0.5-to-400-micron (preferably 0.5 to 25 micron) drug particles are suspended and thoroughly dispersed in the molten polymer in a concentration necessary to give the desired release rate patterns. The polymer is solidified by cooling and ground into small pieces 1 to 200 microns in size.

(C) Intimate mixing

The drug and polymer are dissolved in a common solvent and the solvent is removed in some suitable way (spray-drying, flash-evaporation, etc.). For example: the drug and the polymer are dissolved in the solvent in a 1:1 ratio and to a concentration of 2%. The solvent is flash-evaporated and the resulting film is scraped from the flask and powdered.

The above sustained-release powder, granular or pellet forms may be included in the following type formulations:

(1) Suspensions: Active ingredients of low solubility which have been embedded in or coated with the polymer and are in a finely divided state, 200 microns diameter or less, preferably 50 microns or less, may be suspended in a suitable pharmaceutical vehicle for injection. This vehicle may also contain suspending and thickening agents, e.g., methyl cellulose, and preservatives. These ingredients are combined to give a stable suspension which will release the active ingredient over the time period desired.

(2) Emulsions: Active ingredients insoluble in oil in fine powder form, preferably 10 microns or less, are thoroughly dispersed in a suitable oil, which is, in turn, emulsified in an external aqueous phase (oil in water) using suitable emulsifying agents, e.g., triethanolamine oleate, polyoxyethylene sorbitan monooleate, acacia, gelatin, etc. The aqueous phase may also contain agents such as protective colloids and preservatives, formulated to give a stable emulsion which will provide a controlled release of the active ingredient over the time period desired.

(3) Aqueous suspensions: The active ingredient embedded and/or coated with the polymer in a particle size no greater than 200 microns and preferably no greater than 50 microns is suspended in an aqueous solution which may contain thickening agents, e.g., carboxymethylcellulose; preservatives, e.g., phenol; suspending agents, e.g., polyvinylpyrrolidone; surface active agents; buffers and dextrose or saline to adjust for isotonicity.

(4) Nonaqueous suspensions: The active ingredient embedded and/or coated with the polymer in a particle size usually no greater than 200 microns and preferably no greater than 50 microns is suspended in a suitable oil, etc. The suspension may contain preservatives, e.g., chlorbutanol or methylparaben and propylparaben mixtures, and suspending agents such as aluminum monostearate.

In both the aqueous and nonaqueous preparations, the final product is sterilized by heat, radiation, ethylene oxide or other suitable means prior to use.

The use of absorbable polymer-drug formulations in the controlled administration of fertility control agents over extended periods of time is well-known. U.S. Pat. No. 3,773,919, for example, describes the combination of poly-L-lactide polymers with endocrine agents such as 17$\beta$-estradiol; 2$\alpha$,17$\alpha$-diethynyl-A-nor-5$\alpha$-androstane-2$\beta$,17$\beta$-diol; 17$\beta$-estradiol; 6,6-difluoro-17$\alpha$-ethynyl-17$\beta$-hydroxyestr-4-en-3-one; and 17$\beta$-hydroxyestr- 4-en-3-one adamantane-1'-methanolcarbonate. The poly(alkylene oxalate) polymers of the present invention are effectively substituted for the poly-L-lactide polymers of U.S. Pat. No. 3,773,919 to obtain an alternative polymer-drug composition of similar effect.

What is claimed is:

1. In a pharmaceutical depot composition for parenteral administration of effective amounts of a drug released slowly over an extended period of time which comprises a combination of
   (a) from 1 to 99 percent by weight of composition of a drug in an effective depot amount greater than the single dose amount, and
   (b) a solid, absorbable polymer which is nonreactive toward body tissue and which undergoes biodegradation in the presence of body fluids into products which are metabolized or excreted by the body without adverse body reaction,
the improvement comprising employing as said absorbable polymer a poly(alkylene oxalate) having the formula

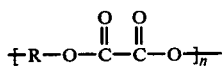

wherein R is a $C_3$ to $C_{16}$ alkylene and n is the degree of polymerization resulting in a polymer inherent viscosity of at least 0.20 determined at 25° C. on a 0.1 g/dl solution of polymer in $CHCl_3$ or hexafluoroisopropanol.

2. The composition of claim 1 wherein R is a $C_4$ to $C_{10}$ alkylene.

3. The composition of claim 1 wherein the ratio of drug to polymer is from 1:4 to 1:20 by weight.

4. The composition of claim 1 wherein the drug is an endocrine agent.

5. The composition of claim 4 wherein the drug is a fertility control agent.

6. The composition of claim 1 in the form of injectable particles dispersed in normal saline or a pharmaceutically acceptable oil.

7. The composition of claim 6 wherein the injectable particles range in size from about 0.1 to 200 microns.

8. The composition of claim 1 in the form of pellets for implantation.

9. The composition of claim 1 wherein the polymer is a mixture of a poly(alkylene oxalate) and at least one other absorbable polymer.

10. The composition of claim 9 wherein the other absorbable polymer is selected from the group consisting of homopolymers and copolymers of lactide and glycolide.

11. The composition of claim 1 wherein the absorbable polymer is a copolymer of $C_3$ to $C_{16}$ alkylene oxalate and at least one other monomer copolymerizable therewith and resulting in an absorbable copolymer.

12. The composition of claim 11 wherein said other monomer is selected from the group consisting of lactide and glycolide.

13. In the process of releasing a controlled effective amount of a parenteral depot drug in an animal or human being over an extended period of time, the improvement comprising administering the composition of claim 1 to said animal or human.

* * * * *